US008757864B2

(12) United States Patent
Yamakawa et al.

(10) Patent No.: US 8,757,864 B2
(45) Date of Patent: Jun. 24, 2014

(54) CHEMICAL ANALYZER

(75) Inventors: Hironobu Yamakawa, Tokyo (JP); Hideo Enoki, Kasumigaura (JP); Isao Yamazaki, Ryugasaki (JP); Nobuhiro Tsukada, Kokubunji (JP)

(73) Assignee: Hitachi High-Technologies Corporation, Tokyo (JP)

( * ) Notice: Subject to any disclaimer, the term of this patent is extended or adjusted under 35 U.S.C. 154(b) by 790 days.

(21) Appl. No.: 11/745,669

(22) Filed: May 8, 2007

(65) Prior Publication Data

US 2007/0264156 A1 Nov. 15, 2007

(30) Foreign Application Priority Data

May 10, 2006 (JP) .................................. 2006-131105

(51) Int. Cl.
*B28C 5/08* (2006.01)
*B28C 5/16* (2006.01)
*B01F 7/00* (2006.01)
*B01F 7/16* (2006.01)
*G01N 31/00* (2006.01)
*B01F 11/00* (2006.01)
*B01F 5/12* (2006.01)

(52) U.S. Cl.
USPC ............... 366/64; 366/65; 366/111; 366/128; 366/212; 366/254; 366/261; 366/267; 366/286; 422/63; 422/64

(58) Field of Classification Search
USPC ............. 366/64, 65, 111, 128, 212, 254, 261, 366/267, 286
See application file for complete search history.

(56) References Cited

U.S. PATENT DOCUMENTS

| 4,705,222 | A | * | 11/1987 | Shohet ............................ 241/69 |
| 4,908,320 | A | | 3/1990 | Zakowski et al. |
| 5,100,242 | A | * | 3/1992 | Latto .............................. 366/267 |
| 5,921,679 | A | * | 7/1999 | Muzzio et al. ................. 366/348 |
| 6,146,592 | A | | 11/2000 | Kawashima et al. |
| 7,188,993 | B1 | * | 3/2007 | Howe et al. .................... 366/111 |
| 2007/0041874 | A1 | * | 2/2007 | Sukavaneshvar et al. ... 422/68.1 |

FOREIGN PATENT DOCUMENTS

| JP | 08-075752 | A | | 3/1996 | |
| JP | 08075752 | A | * | 3/1996 | |
| JP | 8-201395 | | * | 8/1996 | |
| JP | 08201395 | A | * | 8/1996 | ............. G01N 35/02 |

(Continued)

OTHER PUBLICATIONS

Machine translation of JP 08-075752 A.*

(Continued)

*Primary Examiner* — Dirk Bass
*Assistant Examiner* — Jennifer Wecker
(74) *Attorney, Agent, or Firm* — Mattingly & Malur, PC

(57) ABSTRACT

A chemical analyzer supplies a sample and a reagent into a reaction container provided with an opening mixes a fluid which is to be measured and contains the sample and reagent supplied into the reaction container, measures a property of the fluid in the reaction container, and controls the drive for the mixer. The mixer has a vertical drive machine to move the mixing tool up and down. The control unit controls the vertical drive machine to move the mixing tool up and down in the fluid to be measured in the reaction container so as to cause upward and downward flow of the fluid which is to be measured and is positioned below the mixing tool.

8 Claims, 6 Drawing Sheets

(56) References Cited

FOREIGN PATENT DOCUMENTS

| JP | 08-233827 A | 9/1996 |
| JP | 10-062430 | 3/1998 |
| JP | 11-064189 | 3/1999 |

OTHER PUBLICATIONS

Machine translation of JP 08-075752 A, machine translation produced on Mar. 25, 2013.*

* cited by examiner

CHEMICAL ANALYZER

BACKGROUND OF THE INVENTION

1. Field of the Invention

The present invention relates to chemical analyzers and, in particular, to a chemical analyzer provided with a mixing member to mix a small amount of sample-reagent fluid comprising a sample and reagent supplied into a reaction container.

2. Description of the Related Art

A conventional mixing device for automatic analyzers is described in JP-A-10-62430. The mixing device disclosed in JP-A-10-62430 comprises rotating means to drive a mixing bar to rotate and reciprocating means to horizontally reciprocate a support bracket to which the rotating means is set. By both reciprocating and rotating the mixing bar simultaneously within a reaction container, the mixing device mixes a sample and reagents in the reaction container.

In addition, another conventional mixing device for automatic analyzers is described in JP-A-11-64189. The mixing device described in JP-A-11-64189 comprises a vibrating section which vibrates when a voltage is applied thereto, a base section to hold the vibrating section, a mixing bar to mix fluid, a spacer disposed between the base section and the mixing bar and a power supply section to apply the voltage to the vibrating section.

SUMMARY OF THE INVENTION

However, in the above-mentioned mixing device described in JP-A-10-62430, since a fluid comprising a sample and reagent supplied into a reaction container is stirred mainly by horizontal rotating and reciprocating motions, flows occur which are approximately horizontal. Therefore, vertical mixing of the sample-reagent fluid is not efficient. In particular, if the sample tends to be attached in a dot shape to the bottom of the container, it is difficult to mix the sample and the reagent.

Likewise, the above-mentioned mixing device of JP-A-11-64189 makes the backward and forward movements of the vibrating blade to mix a sample-reagent fluid supplied into a reaction container. Thus, similar to the mixing device disclosed in JP-A-10-62430, since flows are substantially limited to the horizontal direction, it is impossible to efficiently make the vertical distributions of the sample and reagent uniform. In particular, if the sample tends to be attached in a dot shape to the bottom of the container, it is difficult to mix the sample and the reagent.

It is an object of the present invention to provide a chemical analyzer in which a sample and reagent supplied into a reaction container can efficiently be mixed by vertically stirring the sample-reagent fluid.

To attain the above-mentioned object, a chemical analyzer according to the present invention comprises: sample supplying means to supply a sample into a reaction container provided with an opening; reagent supplying means to supply a reagent into the reaction container; mixing means having a mixing tool to mix a fluid which is to be measured and is composed of the sample and reagent supplied into the reaction container; measuring means to measure a property of the fluid to be measured in the reaction container; and a control unit to control the drive for the mixing means, wherein: the mixing means has a vertical drive mechanism to move the mixing tool up and down; and the control unit controls the vertical drive mechanism to move the mixing tool up and down in the fluid to be measured in the reaction container so as to cause upward and downward flows of the fluid which is to be measured and is placed below the mixing tool.

Detailed examples of a preferable configuration of the chemical analyzer according to the present invention are as follows:

(1) The mixing tool which is immersed in the fluid to be measured has a flat end whose area is 50% to 90% of the horizontal cross-sectional, internal area of the reaction container.

(2) The mixing tool which is immersed in the fluid to be measured has a slit, a through hole or a mesh structure.

(3) The control unit controls the vertical drive mechanism so that the mixing tool immersed in the fluid to be measured is moved up and down with different frequencies or different amplitudes.

(4) The control unit controls the vertical drive mechanism so that the mixing tool is set in the vicinity of the bottom of the fluid to be measured, moved up and down around the vicinity of the bottom of the fluid with a high frequency and a low amplitude, raised to the vicinity of the center of the fluid to be measured and moved up and down around the vicinity of the center of the fluid with a low frequency and a high amplitude.

(5) The control unit controls the vertical drive mechanism so that after mixing of the fluid to be measured by the mixing tool is completed, the mixing tool is lifted up from the fluid to be measured and vibrated vertically with high frequency and small amplitude.

(6) The upper surface of the mixing tool is tapered so as to make the center higher than the periphery.

(7) The control unit controls the vertical drive mechanism so as to make the descending speed of the mixing tool higher than the ascending speed.

(8) The control unit controls the vertical drive mechanism so that the mixing tool is moved up and down with the top surface kept above the surface of the fluid to be measured and the bottom surface kept dipped in the fluid to be measured.

(9) The bottom surface of the mixing tool is asymmetrical in the depth direction of the reaction container.

(10) The control unit controls the sample supplying means so that the sample is supplied to a position below the bottom surface of the mixing tool in the reaction container.

According to the present invention, it is possible to provide a chemical analyzer in which a sample and reagent supplied into a reaction container can be efficiently mixed by vertically stirring the sample-reagent fluid.

A plurality of embodiments of the present invention will be described below with reference to the drawings. Components of the individual embodiments illustrated in the drawings are given the same reference numeral if they are identical to or correspond to each other. Note that the present invention is not limited to those disclosed in the present specification and may be modified based on what is and will be widely known.

DETAILED DESCRIPTION OF THE PREFERRED EMBODIMENTS

First Embodiment

With reference to FIG. 1 through FIG. 4, the following describes a chemical analyzer, a first embodiment of the present invention.

Figure 1:
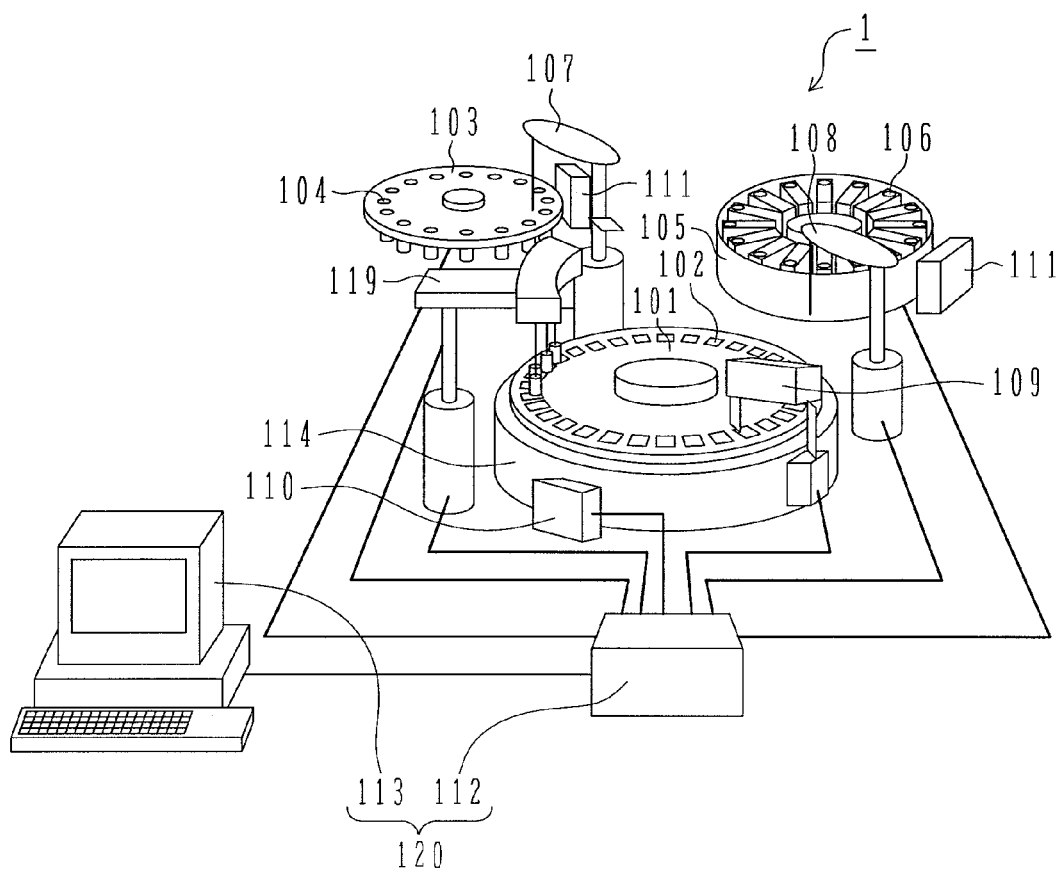
FIG. 1 shows the configuration of a chemical analyzer according to a first embodiment of the present invention.

At first, the following provides a general description of the chemical analyzer 1 or the present embodiment with reference to FIG. 1. FIG. 1 shows the configuration of the chemical analyzer 1 or the first embodiment of the present invention. This chemical analyzer 1 is an apparatus to analyze a small amount of a sample-reagent fluid comprising a sample and reagent. For example, the sample is a biological one containing small amounts of substances of interest.

The chemical analyzer 1 comprises a reaction disk 101, a thermostatic vessel 114, a sample disk 103, a reagent disk 105, a sample dispensing machine 107, a reagent dispensing machine 108, cleaning machines 111, a mixing machine 109, a detecting machine 110, a cleaning machine 119 and a control apparatus 120.

These individual components are configured so that based on information (analysis item, liquid quantity for analysis, etc.) set from a console 113 of the control apparatus 120 before the analysis is started, they operate automatically in a sequential order at predetermined timings according to a program prepared by a controller 112 of the control apparatus 120.

The reaction disk 101 comprises a disk which is rotatably set. The reaction disk 101 has a plurality of reaction container storage sections. These reaction container storage sections are formed at equal intervals along the peripheral rim of the reaction disk 101. Each reaction container 102 is a substantially rectangular very small container with an opening at the top. Set in a reaction container storage section, each reaction container 102 has a small amount of fluid 213 (refer to FIG. 2) supplied therein for measurement. Each reaction container 102 is longer in the radial direction than in the circumferential direction, so that many reaction containers 102 can be set to the reaction disk 101.

Set below the reaction disk 101, the thermostatic vessel 114 has a circular shape with a larger outer diameter than the reaction disk 101. The thermostatic vessel 114 has a ring-shaped water bath 114*a* formed circumferentially and filled with temperature controlled water 204. With reaction containers 102 immersed in this temperature controlled water 204, the thermostatic vessel 114 functions to keep the reaction containers 102 and sample-reagent fluids 213 at a certain temperature.

The sample disk 103 has a disk shape, being rotatably set outside, being arranged in the radius direction of the reaction disk 101. The sample disk 103 has a large plurality of sample container storage sections. These sample container storage sections are formed at equal intervals along the peripheral rim of the sample disk 103. Set in a sample container storage section of the sample disk 103, each sample container 104 contains a sample.

The reagent disk 105 has a cylinder shape, being rotatably set outside, being arranged in the radius direction of the reaction disk 101. The reagent disk 105 has a large number of reagent container storage sections. These reagent storage sections are formed at equal intervals along the peripheral rim of the reagent disk 105. Set in a reagent container storage section of the reagent disk, each reagent container 106 contains a reagent.

The sample dispensing machine 107, which constitutes sample supplying means, has the function to dispense a sample from a sample container 104 into a reaction container 102. The reagent dispensing machine 108, which constitutes reagent supplying means, has the function to dispense a reagent from a reagent container 106 into a reaction container 102.

The mixing machine 109, which constitutes mixing means, has the function to mix a fluid 213 to be measured in a reaction container 102. The fluid to be measured comprises a sample and a reagent which are dispended into the reaction container 102. This mixing machine 109 will be described later in detail.

The detecting means 110, which constitutes measuring means, has the function to measure optical or electrochemical properties, such as absorbency or fluorescence intensity, of the fluid 213 which is to be measured and is a mixture of the sample and the reagent in the reaction container 102, during or after reaction. This detecting means 110 is set around the outer side of the thermostatic vessel 114 so as to face the outer side of each reaction container 102 (namely each fluid 213 to be measured).

The two cleaning machines 111, which constitute cleaning means, have the function to make clean the sample dispensing machine 107 and reagent dispensing machine 108 respectively. The cleaning machine 119, which constitutes cleaning means, has the function to make clean each reaction container 102 after detection (photometric) is completed.

Figure 2:
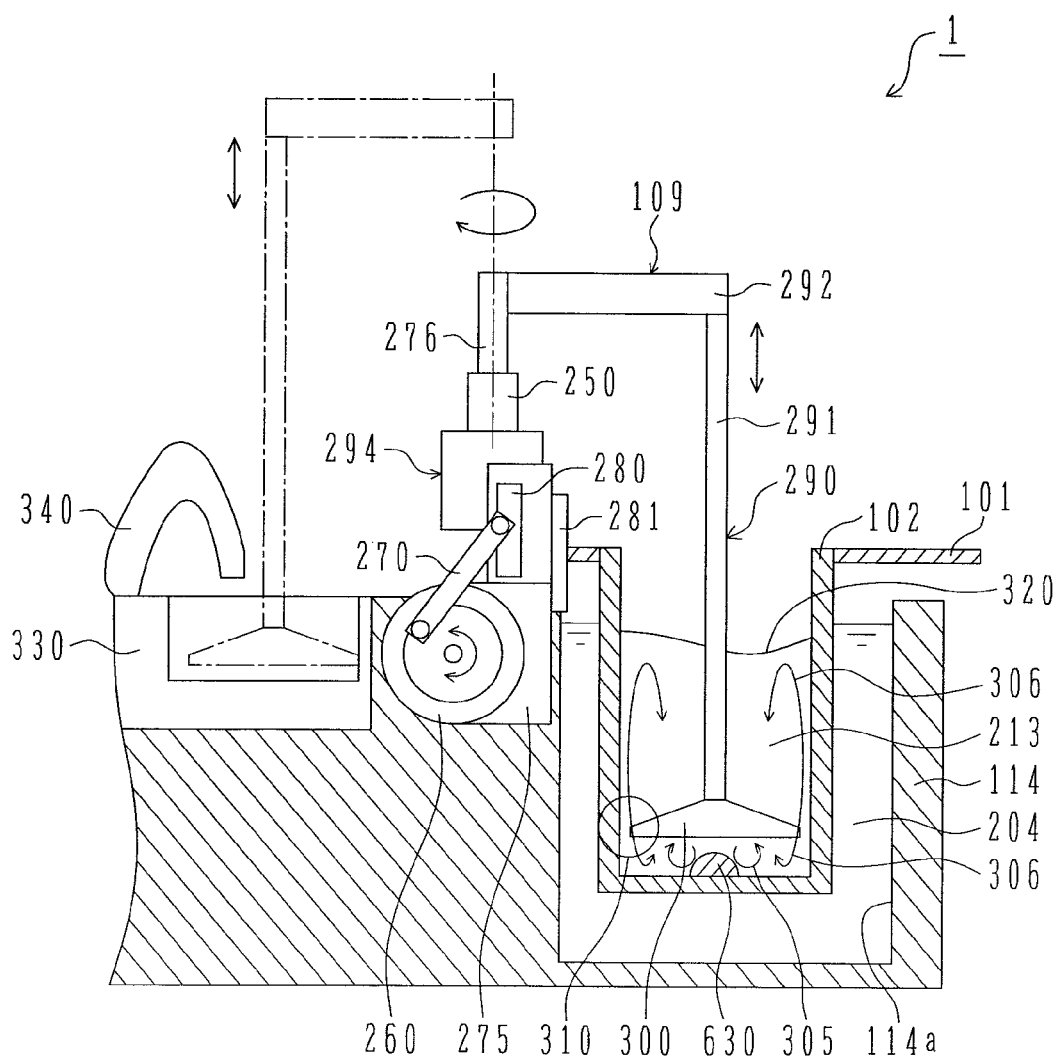
FIG. 2 is a vertical sectional view of a portion of the chemical analyzer of FIG. 1, including a mixing mechanism.
Figure 3:
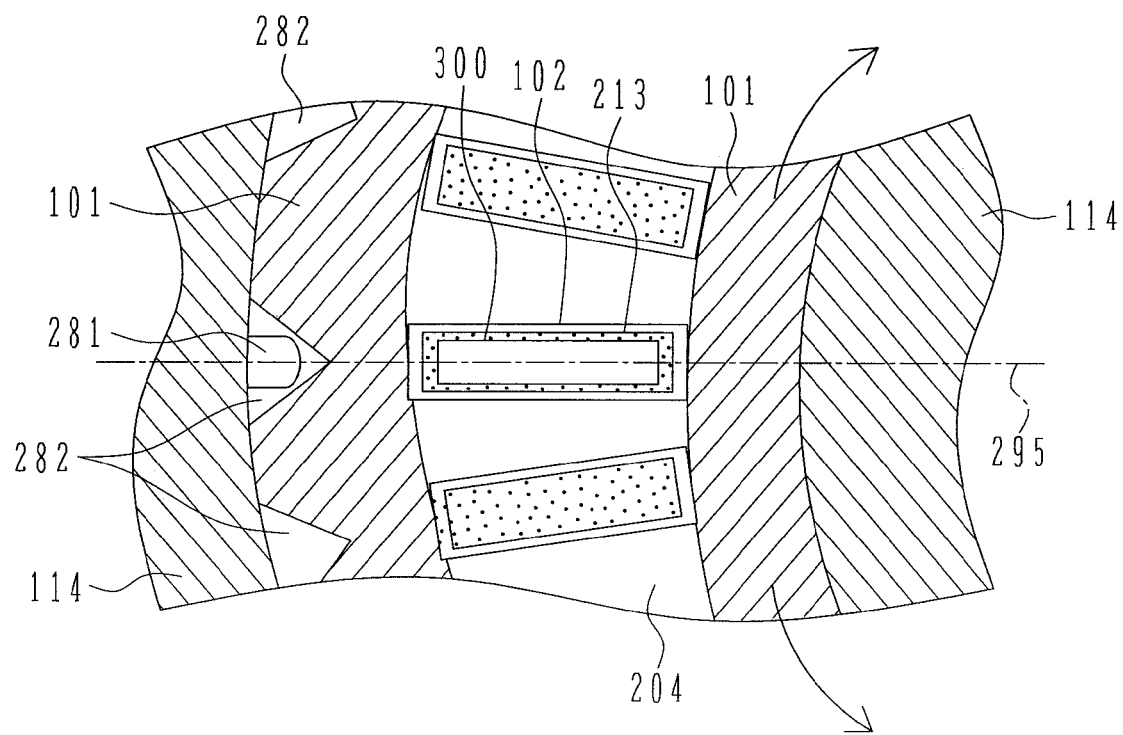
FIG. 3 is a horizontal sectional view of a portion including the mixing mechanism shown in FIG. 2.
Figure 4:
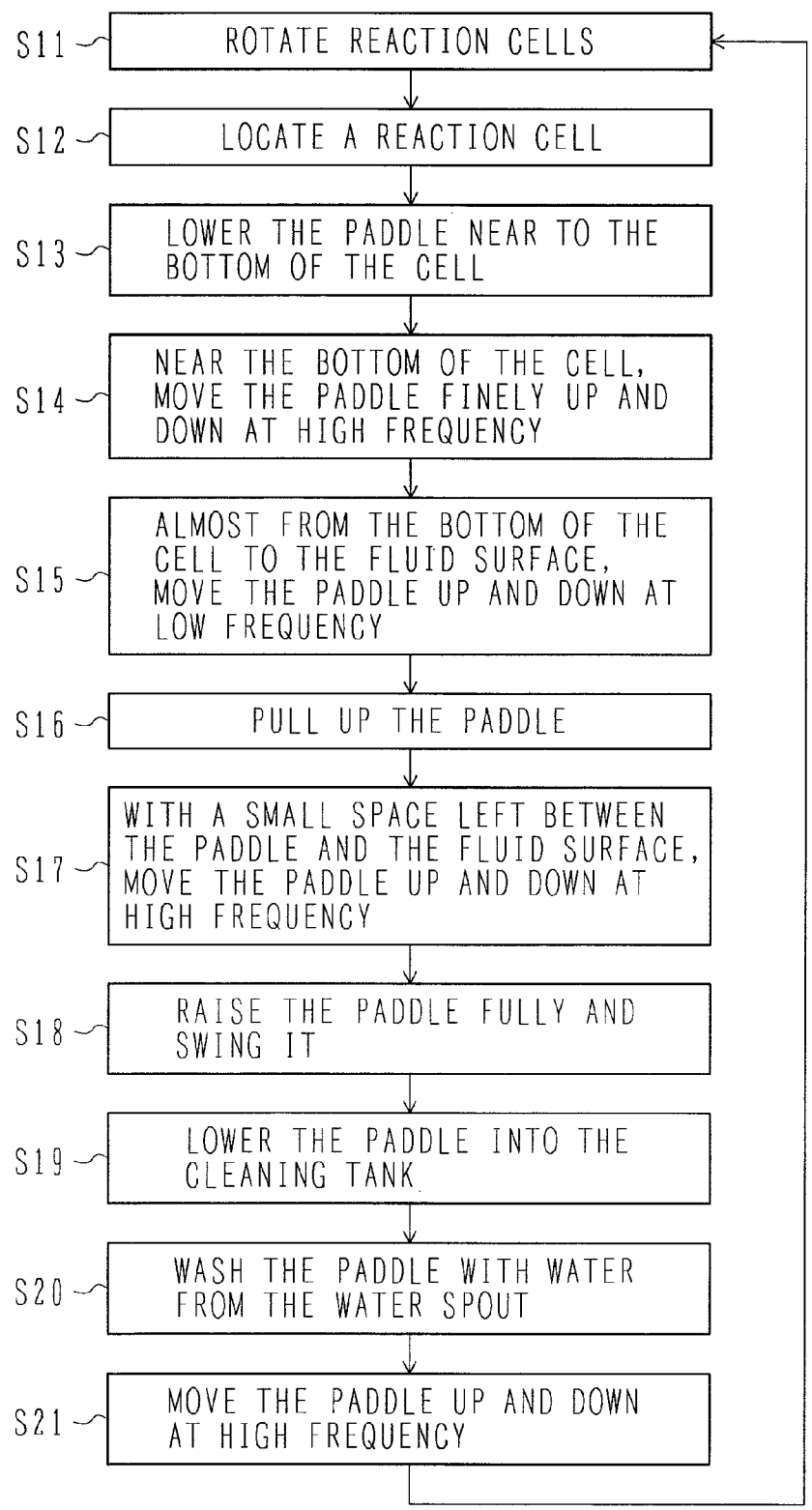
FIG. 4 is a flowchart showing the mixing sequence by the mixing mechanism of FIG. 2.

The following provides a detailed description of the mixing machine 109 with reference to FIGS. 2 to 4. FIG. 2 is a vertical sectional view of a portion of the chemical analyzer 1 shown in FIG. 1, including the mixing mechanism. FIG. 3 is a horizontal sectional view of a portion including the mixing mechanism shown in FIG. 2. FIG. 4 is a flowchart showing the mixing sequence by the mixing machine 109 of FIG. 2.

As described above, the mixing machine 109 is a component to mix/stir a fluid 213 which is to be measured and contains a sample and a reagent in a reaction container 102. Immersed in the temperature controlled water 204, the reaction containers 102 set on the reaction disk 101 are automatically rotated and stopped as the reaction disk 101 is rotated and stopped repeatedly. The mixing machine 109 is programmed to carry out its mixing operation for stirring the fluid 213 when a reaction container 102 is stopped in place.

The mixing machine 109 comprises: a paddle 290 having a paddle plate 300 as a mixing tool and a paddle bar 291; a paddle arm 292; and a drive machine 294 which rotates and raises/lowers the paddle 290 and its arm 292. The drive machine 294 is controlled by the control apparatus 120. The control apparatus 120 controls the drive machine 294 to move the paddle plate 300 upward and downward in the fluid 213 which is to be measured and is contained in the reaction container 102. Since this generates upward and downward flows from and to the zone below the paddle plate 300, high mixing efficiency is attained.

Note that the drive machine 294 uses a rotation motor 250 to provide rotary movement and a lifting motor 260, a crank 270 and a rail 280 to provide vertical movement.

The paddle plate 300, immersed in the fluid 213 to be measured, has a large flat end. Specifically, this flat end occupies 50 to 90% of the horizontal cross-sectional, internal area of the reaction container 102. Therefore, the vertically moving paddle plate 300 can directly apply force to a sample portion 630 of the fluid 213 to be measured, resulting in high efficiency mixing. The sample portion 630 exists around the bottom of the fluid 213. In addition, even if the horizontal cross-section of the reaction container 102 is a very slender rectangle as shown in FIG. 3, it is possible to make the flat end of the paddle plate 300 enough large according to the shape of the reaction container 102 to attain high efficiency mixing by the vertical movement.

While the bottom surface of the paddle plate 300 is flat, the upper surface is tapered so as to make the center higher than the periphery. Therefore, while the sample-reagent fluid 103 below the paddle plate 300 can surely be moved upward by lowering the paddle plate 300, the sample-reagent fluid 213 above the paddle plate 300 can be introduced to the region below the paddle plate 300 smoothly along the tapered surface by raising the paddle plate 300.

The mixing machine 109 mixes a fluid 213 to be measured in such a sequence as shown in FIG. 4.

Firstly, the reaction disk 101 is rotated to move a reaction container 102 filled with a fluid 213 to be measured (step S11). For each reaction container 102, the reaction disk 101 has a notch 282 formed on the circumference thereof. The water bath 114a has an elastic positioning projection 281 provided at a certain position (where mixing of a fluid 213 to be measured in a reaction container 102 is performed).

The reaction container 102 filled with the fluid 213 to be measured is moved to a certain position by the rotated reaction disk 101. There, the reaction container 102 is positioned with regard to the paddle plate 300 as the elastic positioning projection 281 fits into the notch 282 of the reaction disk 101 (step S12) as shown in FIG. 3. This positioning mechanism allows efficient mixing although the reaction container 102 is small and slim and the paddle plate 300 occupies an almost entire opening area of the reaction container 102. This positioning mechanism is set so that the reaction container 102, the paddle plate 300, the notch 282 and the positioning projection 281 have their center lines 295 aligned to each other.

Then, the paddle plate 300 is lowered to immerse it in the fluid 213 to be measured (step S13). Preferably, the clearance 310 between the paddle plate 300 and the side wall of the reaction container 102 is about a twentieth of the battle plate 300. The paddle plate 300 is lowered to the vicinity of the bottom of the reaction container 102. Preferably, the paddle plate 300 is lowered so that the height of the paddle plate 300 from the bottom of the reaction container 102 is about three times the thickness of the paddle plate 300.

The paddle plate 300, immersed in the fluid 213 to be measured as descried above, is vertically vibrated with high frequency and low amplitude (short stroke length) (step S14). Preferably, this vertical moving speed of the paddle plate 300 is at least twice the immersing speed of the paddle plate 300 and the amplitude of vibration is about 20% of the height of the fluid 213 to be measured. Due to the small clearance between the paddle plate 300 and the side wall of the reaction container 102, vertical flows below the paddle plate 300 are largely limited to local flows 305 at the bottom of the reaction container 102. Thus, the sample-reagent fluid 213 below the paddling plate 300, which may contain a sample portion 630 stuck or deposited to the bottom of the reaction container 102, can be intensively moved. In addition, since the flow energy below the paddling plate 300 is dissipated before it reaches to the fluid level 320, it is possible to prevent the fluid level 320 from ruffling at high frequency. Therefore, this step does not have influence on the analytical accuracy since it does not cause contamination, scattering of poorly mixed fluid or the like. Also, the detection accuracy is not influenced since air is not entangled. Preferably, the operating duration is about a half to a fifth of the total mixing time although it depends on the fluid volume, etc.

Then, after raised to a depth of about a half of the total depth of the fluid 213 to be measured, the paddle plate 300 is vertically vibrated with low frequency and high amplitude (step S15). Preferably, this vertical moving speed of the paddle plate 300 is about 50 to 200% of the immersing speed and its amplitude is about 80% of the total depth of the fluid 213 to be measured. The vertical movement of the paddle plate 300 in the fluid 213 to be measured causes global flows 306 across the paddling plate 300, which pass the clearance 310 between the paddling plate 300 and the side wall of the reaction container 102 and go around to the upper and lower surfaces of the paddling plate 300. Since the vertical movement of the paddle plate 300 is slow although the amplitude is large, the fluid level 320 does not greatly undulate. By this operation, the sample-reagent fluid 213 at the bottom of the reaction container 103, which was locally mixed by the previous step, is globally and uniformly mixed in the reaction container 103.

The mixing efficiency can be raised by vertically vibrating the paddle 300 in the sample-reagent fluid 213 with different frequencies and different amplitudes as described above. Note that depending on the type of the sample-reagent fluid, it may be not necessary to repeatedly move the paddle plate 300 up and down. As the case may be, merely immersing the paddle plate 300 in the sample-reagent fluid 213 and pulling it up from the sample-reagent fluid 213 causes large vertical flows, resulting in sufficient mixing.

Then, the paddle plate 300 is pulled up from the sample-reagent fluid 213 (step S16). Set a little above the fluid level, the paddle plate 300 is driven to perform vertical high-frequency small vibrations in order to remove the adherent fluid from the paddle. Preferably, the paddle plate 300 is positioned so that a space of about the thickness of the paddle plate 300 or larger is left between the paddle plate 300 and the fluid level 320 when the paddle plate 300 is at the lowest height. As well, it is preferable to make the ascending motion as slow as possible and the descending motion as fast as possible. To the fluid adhering to the paddle plate 300, this gives large inertial force which acts to return the adherent fluid into the reaction container 102. The fluid on the top surface of the paddle plate 300 runs off easily since the surface is tapered.

It is also preferable to coat the paddle 290 with a water repellent film such as fluorinated resin. This not only reduces adhesion of the sample-reagent fluid 213 onto the paddle plate 300 when the paddle plate 300 is pulled up from the sample-reagent fluid 213 but also contributes to raising the mixing efficiency since the drag force acting on the paddle plate 300 in the sample-reagent fluid 213 is lowered and therefore the paddle driving power can be reduced. Further, even if air bubbles are formed from the air entangled by the undulating fluid surface 320, these air bubbles can be removed since the low-wettability surface tends to gather them. This contributes to raising the detection accuracy.

Then, as indicated by the dashed lines in FIG. 2, the paddle plate 300 is raised fully and swung (step S18) and placed in a cleaning tank 330 (step S19). To the paddle plate 300 therein, washing water is poured from a water spout 340 (step S20). While washing water is being poured, the paddle plate 30 is moved up and down in order to raise the washing effect by facilitating flows. Then, after the washing water is stopped and the washing is completed, the paddle plate 330, which is either pulled up from or left in the washing tank 330, is driven to perform vertical high-frequency small vibrations in order to remove the adherent washing water from the paddle plate 300 (step S21). Similar to the previous step of small vibrations, the ascending motion is slow while the descending motion is fast, making it possible to send adherent washing water to the washing tank 330.

According to the configuration and operation described so far, it is possible to provide a chemical analyzer with a mixing unit which is simple in structure and superior in mixing efficiency, contamination control, etc.

Second Embodiment

Figure 5:
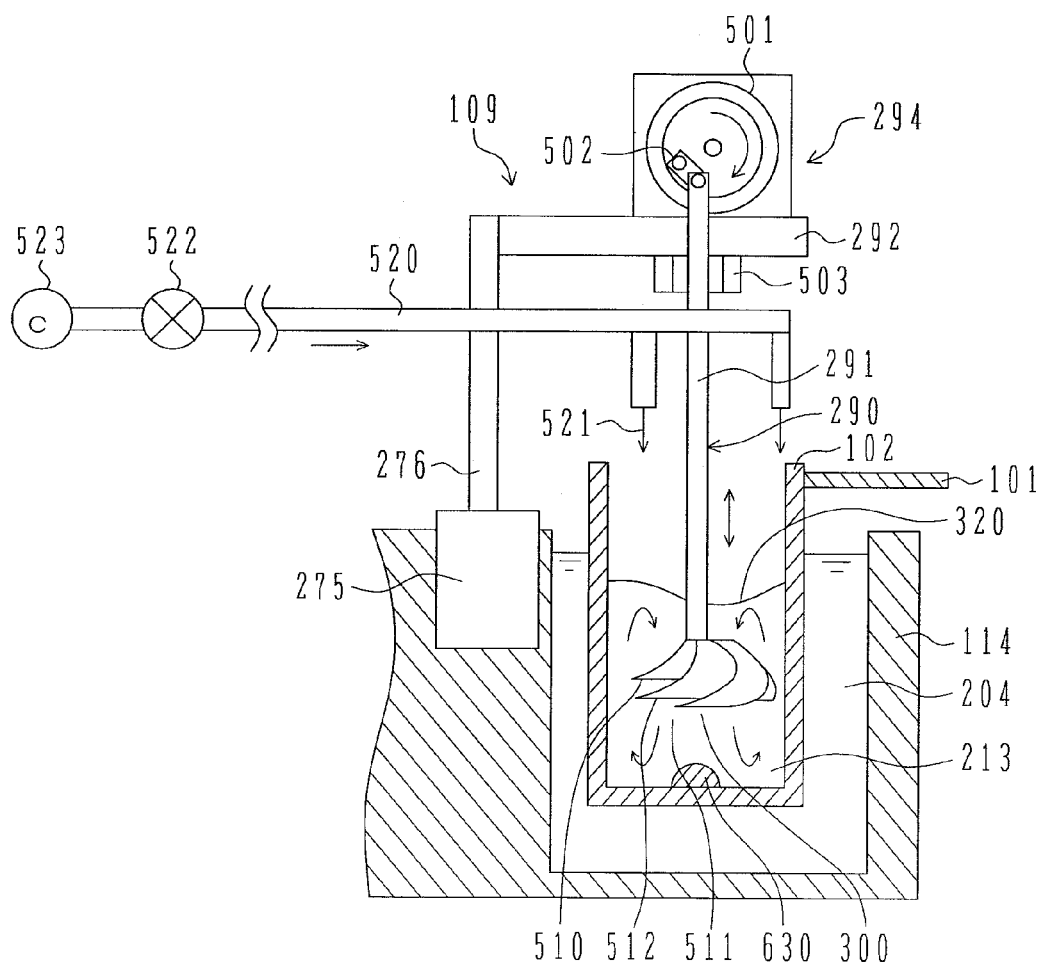
FIG. 5 is a vertical sectional view of a portion of a chemical analyzer according to a second embodiment of the present invention, including a mixing mechanism.

With reference to FIG. 5, the following describes a chemical analyzer 1 according to a second embodiment of the present invention. FIG. 5 is a vertical sectional view of a portion of the chemical analyzer 1 shown in FIG. 1, including the mixing mechanism. Except for difference described below, the second embodiment is substantially the same as the first embodiment. Duplicated description is avoided.

In the second embodiment, a paddle arm 292 is supported by a support shaft 276 which is extended from a support base 275 on the analyzer. A drive machine 294 for a paddle 290 comprises a lifting motor 501 and a crank 502 and provides only the function to move the paddle 290 up and down. A paddle bar 291 moves through a paddle guide 503.

A paddle plate 300 has a plurality of openings 510. Moving the paddle up and down generates flows 511 which go through the openings 510. In this process, strong shearing force by the openings 510 helps attain effective mixing. The openings 510 may be realized either by forming through holes in the paddle plate 300 or forming a meshwork-like paddle plate 300. Further, as shown in FIG. 5, the paddle plate 300 may be formed by arranging a plurality of twisted plates as paddle blades 512, which generate spiral flows to raise the mixing efficiency.

After the mixing is performed, the paddle 300 is raised to such a height that it is a little above the fluid surface 320. Then, air blows 521 are given from an air tube 520 attached to the paddle arm 292. The chemical analyzer is provided with a compressor 523 which supplies pressure to send water for washing the dispensing machine 107 and others. Since the air tube 520 is connected to the compressor 523 via a valve 522, it is possible to give air blows 521 when the paddle 300 is pulled up. Since the fluid left in the openings 510 of the paddle plate is blown off into the reaction container 102, the sample-reagent fluid 213 is not taken away or does not cause contamination in any other place.

Third Embodiment

Figure 6:
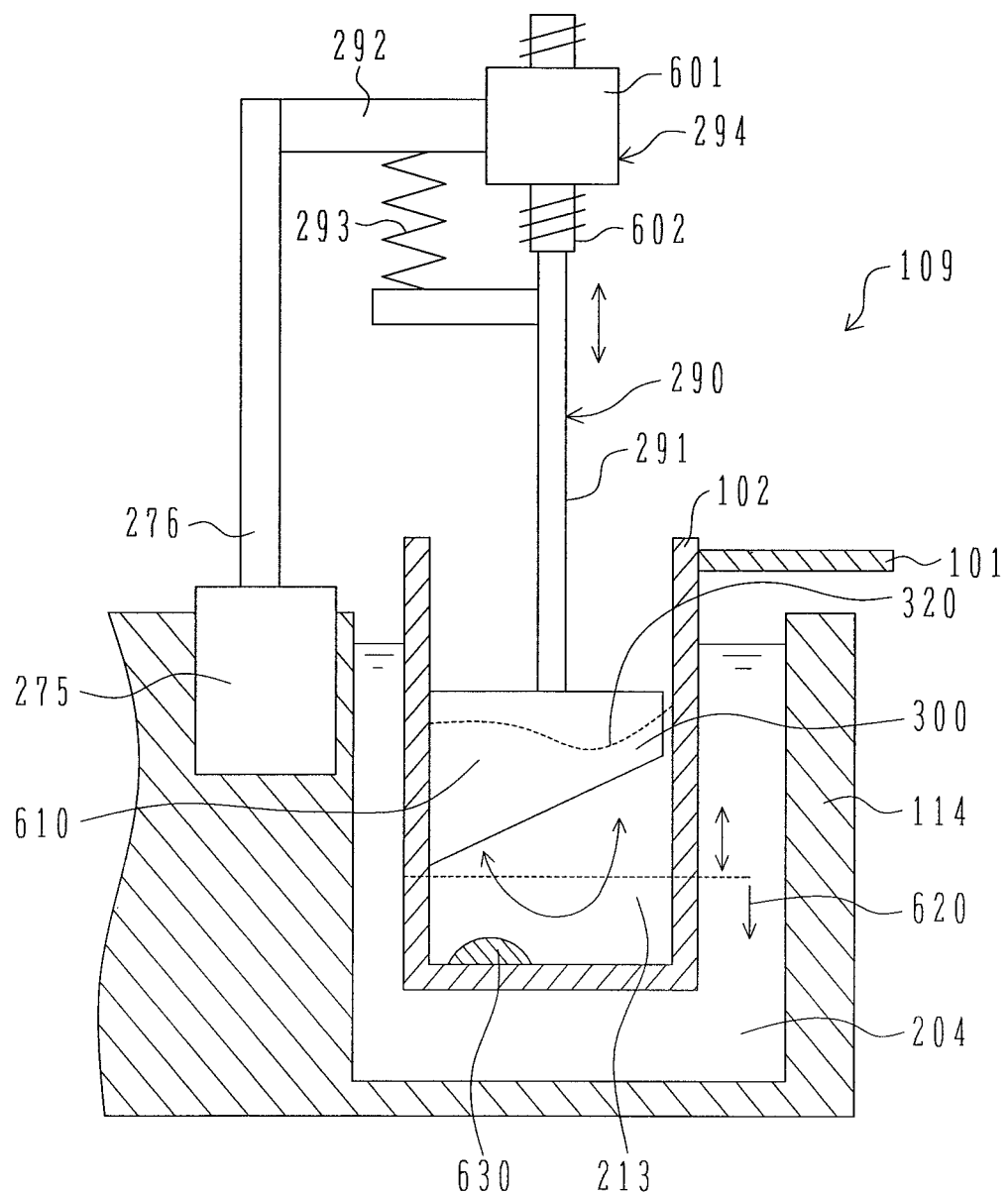
FIG. 6 is a vertical sectional view of a portion of a chemical analyzer according to a third embodiment of the present invention, including a mixing mechanism.

With reference to FIG. 6, the following describes a chemical analyzer 1 according to a third embodiment of the present invention. FIG. 6 is a vertical sectional view of a portion of the chemical analyzer 1 shown in FIG. 1, including the mixing apparatus. Except for differences described below, the third embodiment is substantially the same as the first embodiment. Duplicated description is avoided.

The mixing machine 109 is a mechanism to mix/stir a fluid 213 which is to be measured and contains a sample and reagent in a reaction container 102. The mixing machine 109 comprises a paddle 290, a drive machine 294 to move the paddle 290 up and down and a paddle arm 292 supported by a support shaft 276 which is extended from a support base 275 on the analyzer. The vertical drive machine 294 comprises a screw type motor 601 and a spring 293 which are mounted on the paddle arm 292. The paddle bar 291 is in contact with a screw 602 and can move independently. Pushed downward by the screw 602 and held upward by the spring 293, the paddle bar 291 is moved up and down.

The paddle plate 300 is positioned with its one side surface kept in contact with a side wall 610 of a reaction container 102. The paddle plate 300 is moved vertically along the container's side wall 610 to mix a fluid 213 to be measured. The bottom surface of the paddle plate 300 is asymmetrical in the depth direction of the reaction container 102. In the case of FIG. 2, the left side is projected downward while the right side is dented. Due to this shape, the sample-reagent fluid 213 tends to move to the dented space, causing a large flow. In addition, the sample-reagent fluid 213 has uneven disordered flows which allow higher efficient mixing than simple regular flows. Thus, it is desirable that a sample portion 630 appears near the side wall of the container rather than at the center. If so, the sample portion is easier to be moved due to the asymmetry of flows, resulting in higher efficiency mixing.

The paddle's stroke range is set so that it doesn't enter an optical detection region 620 which is assumed at the bottom of the container as a region to receive detection light. Therefore, the detection accuracy is not influenced. Preferably, the paddle plate 300 is moved up and down near the fluid surface so that only a part of the paddle plate 300 is dipped in the fluid. This reduces the amount of fluid to be taken away and suppresses the consequent influence on the contamination control. In this case, flows do not cause the fluid surface 320 to excessively undulate although the asymmetrical shape is employed.

What is claimed is:

1. A chemical analyzer comprising:
   means for supplying a sample into a reaction container provided with an opening;
   means for supplying a reagent into the reaction container;
   a mixing tool having a plate with a substantially flat bottom surface to mix a fluid to be measured that contains a sample and a reagent, a sample and a reagent being supplied into the reaction container;
   means for measuring a property of a fluid in the reaction container; and
   a control unit for controlling driving of the mixing means,
   a vertical drive mechanism to move the mixing tool up and down,
   wherein the control unit controls the vertical drive mechanism and is programmed to immerse the mixing tool into a fluid in the reaction container at an immersion speed and to move the mixing tool up and down in a fluid in the reaction container so as to cause upward and downward flows of a fluid which is disposed below the mixing tool, and
   wherein the control unit controls the vertical drive mechanism and is programmed to position the substantially flat bottom surface of the mixing tool in a vicinity of a bottom of the reaction container to mix a fluid, and to move the mixing tool up and down in the vicinity of the bottom of the reaction container with a first frequency in which the mixing tool moves at least twice the immersion speed and with a first vibration amplitude that is about 20% of a height of a fluid in the reaction container to intensively move a portion of a sample that is at the bottom of the reaction container by local flows of a fluid at the bottom of the reaction container, and
   wherein the control unit controls the vertical drive mechanism and is programmed to raise the substantially flat bottom surface of the mixing tool to a vicinity of a center of a fluid in the reaction container and to move the mixing tool up and down around the vicinity of the center of a fluid with a second frequency in which the mixing tool moves at 50 to 200% of the immersion speed and with a second vibration amplitude that is about 80% of a height of a fluid in the reaction container to globally and uniformly mix a portion of a sample which was previously locally mixed by the local flows at the bottom of the reaction container.

2. The chemical analyzer according to claim 1, wherein the control unit controls the vertical drive mechanism and is configured, after mixing of the fluid in the reaction container by use of the mixing tool is completed, to pull the mixing tool to above a surface of a fluid in the reaction container and to vibrate the mixing tool vertically with a high frequency and a low amplitude in order to remove the adherent fluid from the mixing tool.

3. The chemical analyzer according to claim 1, wherein the control unit controls the vertical drive mechanism so as to make a descending speed of the mixing tool higher than an ascending speed of the mixing tool.

4. The chemical analyzer according to claim 1, wherein the control unit controls the vertical drive mechanism so that the mixing tool is moved up and down with a top surface of the mixing tool kept above the surface of a fluid in the reaction container and the substantially flat bottom surface of the mixing tool kept immersed in a fluid in the reaction container.

5. A method for a chemical analyzer, comprising:
supplying a sample into a reaction container provided with an opening;
supplying a reagent into the reaction container;
controlling a vertical drive mechanism to insert a mixing tool having a plate with a substantially flat bottom surface into the reaction container positioned below the mixing tool, the reaction container containing a fluid including the sample and the reagent to be measured in the reaction container;
controlling the vertical drive mechanism to immerse the mixing tool into a fluid in the reaction container at an immersion speed and to position the mixing tool in the vicinity of the bottom of the fluid to be measured;
controlling the vertical drive mechanism to move the substantially flat bottom surface of the mixing tool up and down in the vicinity of the bottom of the reaction container with a first frequency in which the mixing tool moves at least twice the immersion speed and with a first vibration amplitude that is about 20% of a height of a fluid in the reaction container to intensively move a portion of the sample that is at a bottom of the reaction container by local flows of the fluid at the bottom of the reaction container; and
controlling the vertical drive mechanism to raise the substantially flat bottom surface of the mixing tool to the vicinity of the center of the fluid in the reaction container and to move the mixing tool up and down around the vicinity of the center of the fluid with a second frequency in which the mixing tool moves at 50 to 200% of the immersion speed and with a second vibration amplitude that is about 80% of a height of a fluid in the reaction container to globally and uniformly mix the portion of the sample which was previously locally mixed by the local flows at the bottom of the reaction container.

6. The method according to claim 5, further comprising:
controlling the vertical drive mechanism, after mixing of the fluid by use of the mixing tool is completed, to pull the mixing tool to above a surface of the fluid and to vibrate the mixing tool vertically with a high frequency and a low amplitude in order to remove the adherent fluid from the mixing tool.

7. The method according to claim 5, further comprising:
controlling the vertical drive mechanism such that a descending speed of the mixing tool is higher than an ascending speed of the mixing tool.

8. The method according to claim 5, wherein the mixing tool is moved up and down with a top surface of the mixing tool kept above the surface of the fluid to be measured and the substantially flat bottom surface of the mixing tool kept immersed in the fluid to be measured.

* * * * *